(12) United States Patent
Hayes-Gill et al.

(10) Patent No.: US 12,685,463 B2
(45) Date of Patent: Jul. 21, 2026

(54) PPG MEASUREMENT

(71) Applicant: SUREPULSE MEDICAL LIMITED, Derby (GB)

(72) Inventors: Barrie Hayes-Gill, Derby (GB); James Carpenter, Derby (GB)

(73) Assignee: SUREPULSE MEDICAL LIMITED, Derbyshire (GB)

( * ) Notice: Subject to any disclaimer, the term of this patent is extended or adjusted under 35 U.S.C. 154(b) by 971 days.

(21) Appl. No.: 17/792,296

(22) PCT Filed: Jan. 13, 2021

(86) PCT No.: PCT/GB2021/050076
§ 371 (c)(1),
(2) Date: Jul. 12, 2022

(87) PCT Pub. No.: WO2021/144570
PCT Pub. Date: Jul. 22, 2021

(65) Prior Publication Data
US 2023/0039857 A1 Feb. 9, 2023

(30) Foreign Application Priority Data

Jan. 13, 2020 (GB) ..................................... 2000438
Jan. 15, 2020 (GB) ..................................... 2000567

(51) Int. Cl.
*A61B 5/1455* (2006.01)
*A61B 5/00* (2006.01)
*A61B 5/024* (2006.01)

(52) U.S. Cl.
CPC ............ *A61B 5/14552* (2013.01); *A61B 5/68* (2013.01); *A61B 5/02416* (2013.01)

(58) Field of Classification Search
CPC ... A61B 5/14552; A61B 5/68; A61B 5/02416; A61B 2562/0219; A61B 5/6814;
(Continued)

(56) References Cited

U.S. PATENT DOCUMENTS 5,237,994 A * 8/1993 Goldberger ........ A61B 5/14552
600/323
6,035,223 A 3/2000 Baker, Jr.
(Continued)

FOREIGN PATENT DOCUMENTS

EP 3403574 A1 11/2018
GB 2572626 A 10/2019
(Continued)

OTHER PUBLICATIONS

International Search Report and Written Opinion from corresponding PCT Appln. No. PCT/GB2021/050076, mailed Mar. 18, 2021. 13 pages.

(Continued)

*Primary Examiner* — Abid A Mustansir
(74) *Attorney, Agent, or Firm* — Secant IP, PLLC; Donald J. Perreault

(57) ABSTRACT

A device is disclosed comprising: an optical physiological sensor and a further measurement system. The optical physiological sensor comprises a light emitter and a light detector configured to detect the light from the light emitter after it has been attenuated by tissue comprising blood vessels. The optical physiological sensor is configured to determine the value of a physiological parameter from the detected light. The further measurement system is configured to determine when the value of the physiological parameter is likely to be reliable. The further measurement system comprises at least one measurement subsystem, each measurement subsystem employing a different measurement modality that is also different to a measurement modality used to determine the value of the physiological parameter.

19 Claims, 9 Drawing Sheets

(58) Field of Classification Search
CPC . A61B 5/0059; A61B 5/14553; A61B 5/1495;
A61B 5/277; A61B 5/6843; A61B
5/7221; A61B 5/7225; A61B 5/6803
See application file for complete search history.

(56) References Cited

U.S. PATENT DOCUMENTS

| | | | | |
|---|---|---|---|---|
| 10,874,348 | B1 * | 12/2020 | Han | A61B 5/6843 |
| 2010/0076282 | A1 | 3/2010 | Sandmore | |
| 2010/0081904 | A1 * | 4/2010 | Medina | A61B 5/6814 |
| | | | | 600/323 |
| 2012/0029345 | A1 * | 2/2012 | Mahfouz | A61B 5/743 |
| | | | | 600/595 |
| 2015/0245782 | A1 | 9/2015 | Morland et al. | |
| 2016/0192716 | A1 * | 7/2016 | Lee | G06F 1/163 |
| | | | | 2/243.1 |
| 2017/0027521 | A1 | 2/2017 | Geva et al. | |
| 2017/0215747 | A1 * | 8/2017 | van Dinther | A61B 5/6826 |

FOREIGN PATENT DOCUMENTS

| | | | |
|---|---|---|---|
| WO | 2014020484 | A2 | 2/2014 |
| WO | 2015171667 | A1 | 11/2015 |
| WO | 2017149325 | A1 | 9/2017 |
| WO | 2019197878 | A1 | 10/2019 |

OTHER PUBLICATIONS

Examination Report under Section 18(3) of United Kingdom Application No. GB2000567.4, dated Feb. 11, 2021, 3 pages.

* cited by examiner

| | | |
|---|---|---|
| —— | sensor upward | SU |
| —— | sensor downward | SD |
| —— | sensor fold over | SF |
| —— | head loose | CL |
| —— | head tight | CT |

Ratio of DC Infared over DC Red and DC Green over DC Red

Head

PPG MEASUREMENT

FIELD

The present invention relates to pulse oximetry. In particular, the invention relates to improvements in the accuracy and reliability of SpO$_2$ measurements in new-borns (neonates).

BACKGROUND

When a heart beats, a cardio pulse circulates around the body. If the skin is irradiated with light (visible or non-visible), a light level is returned that comprises a non-varying and varying component. When the cardio pulse arrives, more light is absorbed in the increasing blood volume and, as a result, the level of light detected is reduced. The time-varying optical signal that is detected is called the Photoplethysmogram (PPG). The PPG is an AC signal related to the heart rate and 'sits' on top of a (non-varying) DC signal caused by the non-moving haemoglobin, skin and bone absorption.

The detection of the PPG depends upon the wavelength of the light, the separation between the source and detector, the deployment of either reflection or transmission, temperature, and physiological conditions.

By measuring a PPG at different wavelengths, a level of oxygen saturation in the haemoglobin can be detected due to the different absorption coefficient of Hb (de-oxygenated haemoglobin) and HbO$_2$ (oxygenated haemoglobin) as a function of wavelength either side of the isosbestic point, at approximately 800 nm (see FIG. 1).

WO 2017/149325 (A1) discloses a hat, and a monitoring system, for a neonate, particularly for monitoring the physiological condition (such as blood oxygen saturation (e.g. SpO$_2$)) of the neonate. The hat disclosed therein comprises: a central portion, a first side portion and second side portion attached to opposite sides of the central portion, a first fastener; a top flap and a second fastener. The hat has an unfolded configuration and a worn configuration. In the unfolded configuration the first and second portions extend away from each other from the central portion in opposite directions. In the worn configuration the hat wraps a neonate's head with the central portion in contact with the back of the neonate's head, the first portion wrapped around a first side of the neonate's head and the second portion wrapped around a second side of the neonate's head. The first and second portions are configured to be fastened together in the worn configuration by the first fastener so that the first portion, central portion and second portion together define a hat rim encircling the neonate's head. The top flap is configured to cover the top of the neonate's head in the worn configuration. The top flap is configured to be fastened to at least one of the first, central and second portions by the second fastener. The hat may further comprise an optical physiological sensor that may comprise: a flexible circuit board, a light emitter and a light detector; the flexible circuit board having: a sensor portion to which the light emitter and light detector are connected; a module portion including contacts for electrically connecting the light emitter and light detector to a removable readout module; and an elongate lead portion between the sensor portion and module portion. The optical physiological sensor is held in contact with the head of the neonate when the hat is in the worn configuration. In order to obtain a reliable PPG (and SpO$_2$) measurement, proper placement of the sensor on the head is necessary, with the correct amount of contact pressure. Too little contact pressure may lead to movement artefacts (e.g. due to the sensor lifting during movement), and too much may lead to blanching of the skin.

The Perfusion Index is the ratio of the varying and non-varying components of light from the skin (i.e. PPG/DC). SpO$_2$, the peripheral oxygen saturation (an estimate of the oxygen saturation level in the blood), is related to the ratio of Perfusion Index (PI) measured using red light and IR. SpO$_2$ may be determined by pulse oximetry using the following formula:

$$R = \frac{PPG_{red}/DC_{red}}{PPG_{IR}/DC_{IR}}$$

$$SpO_2 = f(R)$$

where f(R) relates the R value to the SpO2 value, and is empirically determined by calibration for a particular sensor (and may depend upon the source and detector separation), $PPG_{red}$ is the pulsatile component of the detected red light (after absorption by tissue), $DC_{red}$ is the non-varying component of the detected red light (after absorption by tissue), $PPG_{IR}$ is the pulsatile component of the detected infra-red light (after absorption by tissue), $DC_{red}$ is the non-varying component of the detected infra-red light (after absorption by tissue). Example wavelengths for the red and IR light are 660 nm and 940 nm respectively (but other wavelengths may also be used).

In the stratum corneum, the epidermis, and the underlying physiology (i.e. muscle, cartilage, ligaments etc.), both the PPG and the DC (both human and animal) are strongly dependent on the various spatial locations on the body (resulting in spatial PPG and DC variability) and micro skin variations (resulting in temporal PPG and DC interference with movement artefacts of the detector and light source relative to the skin). These variations can make it difficult to obtain reliable PPG and SpO2 measurements.

It is therefore desirable to improve the reliability of PPG measurement and hence SpO$_2$ measurement in various critical circumstances, particularly for neonatal care, where it may be necessary to monitor SpO$_2$ in order to determine if resuscitation is required. Such improvements may help to decrease the mortality rate of neonates.

SUMMARY

According to a first aspect, there is provided a device (e.g. a photoplethysmography device) comprising:

an optical physiological sensor, wherein the optical physiological sensor comprises a light emitter and a light detector configured to detect the light from the light emitter after it has been attenuated by tissue comprising blood vessels, and the optical physiological sensor is configured to determine the value of a physiological parameter from the detected light;

a further measurement system configured to determine when the value of the physiological parameter is likely to be reliable, the further measurement system comprising at least one measurement subsystem, each employing a different measurement modality that is also different to a measurement modality used to determine the value of the physiological parameter.

The at least one measurement subsystem may comprise at least a first and a second measurement subsystem.

The further measurement system may comprise a measurement subsystem configured to determine a DC light ratio of a non-varying component of detected light of a first wavelength and a second different wavelength after attenuation by the tissue.

The first wavelength may correspond with green light, and the second wavelength may correspond with red light or infra-red light.

The device may be configured to determine an optimum pressure of the device against the tissue using the DC light ratio.

The further measurement system may comprise a measurement system that includes a capacitive sensor having an electrode configured to come into contact with the tissue.

The capacitive sensor may comprise a pressure-sensitive capacitive sensor.

The pressure-sensitive capacitive sensor may comprise a pair of electrodes and a compressible dielectric sandwiched between the electrodes.

The capacitive sensor may comprise a plurality of capacitive sensors, wherein each of the capacitive sensors is disposed at a different location proximate the optical physiological sensor.

The further measurement system may comprise a measurement subsystem that includes a pressure or force sensor.

The pressure or force sensor comprises a plurality of pressure or force sensors, each disposed at a different location around the optical physiological sensor.

The device may comprise a detector lens between the light detector and the tissue, and an illumination lens between the light emitter and the tissue.

The optical physiological sensor may comprise a photoplethysmogram (PPG) sensor and/or a pulse oximeter.

The light emitter may comprise a plurality of light-emitting diodes (LEDs).

The light detector may comprise a photodiode.

According to a second aspect, there is provided a hat comprising the device according to the first aspect, wherein the hat is configured to retain the device with the optical physiological sensor in contact with the forehead of a patient.

The hat may be sized to fit a neonate.

The hat may be in accordance with the disclosure of WO 2017/149325, including any of the optional features thereof.

According to a third aspect, there is provided a method of determining am optical physiological measurement with a photoplethysmography device, comprising:

illuminating a portion of tissue;

detecting light after it has been attenuated by the tissue;

determining the optical physiological measurement from the detected light;

using at least one further measurement system to determine when the physiological measurement is likely to be reliable.

The optical physiological measurement may comprise a PPG or SpO2 measurement.

Using the further measurement system may comprise at least one, or at least two of:

i) determining a DC light ratio of a non-varying component of detected light of a first wavelength and a second different wavelength after attenuation by the tissue;

ii) using a capacitive sensor to detect proper contact with the tissue;

iii) using a pressure sensor to detect proper contact.

A detector lens may be disposed between a light detector and the tissue, and an illumination lens may be disposed between a light emitter and the tissue.

The method may comprise automatically indicating or flagging whether the optical physiological measurement can be trusted in dependence on an output from the further measurement system.

Features of each aspect may be combined with those of any other aspect. For example, the method of the third aspect may be performed using the device of the first aspect (including any of the optional features thereof) or the hat of the second aspect. The device of the first aspect or the hat of the second aspect may be configured to perform the method of the third aspect, including any of the optional features thereof.

BRIEF DESCRIPTION OF THE DRAWINGS

The invention is described in further detail below by way of example and with reference to the accompanying drawings, in which.

DETAILED DESCRIPTION

Figure 1:
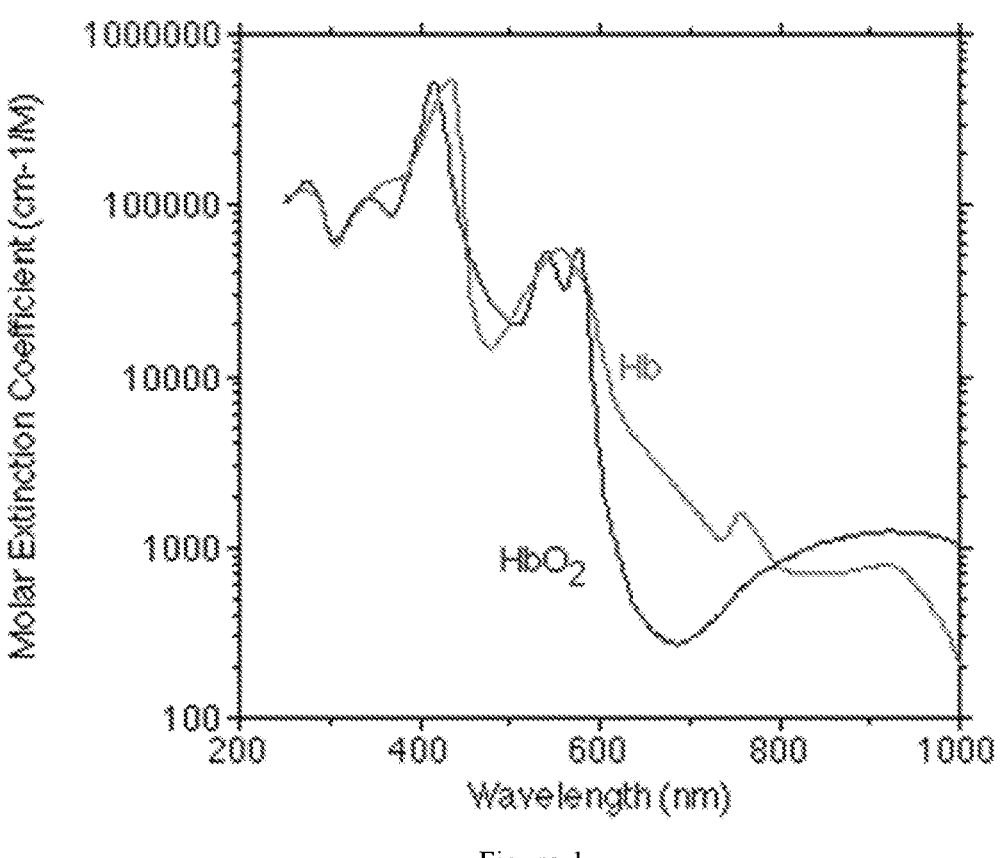
FIG. 1 shows an example of an absorption spectrum of deoxyhemoglobin (Hb) and oxyhemoglobin ($HbO_2$), taken from "Optical Absorption of Hemoglobin" by Scott Prahl (https://omlc.org/spectra/hemoglobin/)

FIG. 1 shows an example of an absorption spectrum of deoxyhemoglobin (Hb) and oxyhemoglobin (HbO$_2$). As discussed above, by using the detection of the PPG at different wavelengths it is possible to detect the level of oxygen saturation in the haemoglobin due to the different absorption coefficient of Hb and HbO$_2$ as a function of wavelength either side of the isosbestic point, at approximately 800 nm.

The optical signature of skin may be used to determine when an optical physiological sensor is appropriately positioned to determine a reliable PPG or SpO2 measurement. By understanding and accounting for optical features of the skin, it may be possible to generate a more reliable PPG and hence to more reliably determine SpO$_2$ values in various critical circumstances.

Certain embodiments provide a multimodal method for detecting when the PPG and DC signals can be trusted in order to present the user with an accurate and reliable SpO$_2$ value, and increase the user's confidence in the value of the SpO$_2$ value that is obtained.

An accelerometer may be used to determine if the sensor is subject to motion. However, accelerometers may be relatively large and usually make the sensor unwieldy. Even with miniature devices, additional wires are often required and the resulting electromagnetic interference can seriously affect the detection of the small photocurrents from the PPG and DC signals.

It has been found that by combining two or more of five different techniques (or modes or modalities), which is discussed in more detail below, surprising results may be obtained. The results that are obtained may be used to determine if a hat (comprising a sensor) is fitted correctly on a subject (such as a neonate). This may greatly improve the accuracy and reliability of a PPG signal measurement and/or an SpO$_2$ measurement. The five techniques may be categorised as follows: 1) the measurement of a DC light ratio at different wavelengths; 2) the detection of human capacitance; 3) the detection of a change in capacitance of a sensor with pressure; 4) the detection of a piezoelectric force; and 5) the employment of lens-based opto-spatial reduction.

Using only one of the techniques listed above may not produce the desired effect of knowing if an optical physiological sensor is positioned properly to obtain reliable sensors. In the context of a hat based sensor, similar to that disclosed in WO 2017/149325 the techniques can be used to assess whether the cap is fitted correctly. A combination of two or more of the techniques may be used to determine if the cap is fitted correctly and hence that the sensor is positioned correctly on the subject (e.g. the head of a neonate).

There are several possible advantages of combining two or more of the techniques listed above. Additional sensing modalities (e.g. pressure, capacitance, DC light ratios etc) may provide an attending team with contextual information which may be used when adjusting position and or the tightness of a hat in order to avoid occlusion and tilting. Any motion that is detected via one, two or more alternative sensing modalities may allow a real-time SpO$_2$ measurement to remove rogue data and to attach a confidence flag to the measurement data. A log of any motion that is detected may allow significant post-processing assistance.

Each of the five techniques listed above is discussed in more detail below.

1) The Measurement of a DC Light Ratio at Different Wavelengths

Figure 2:
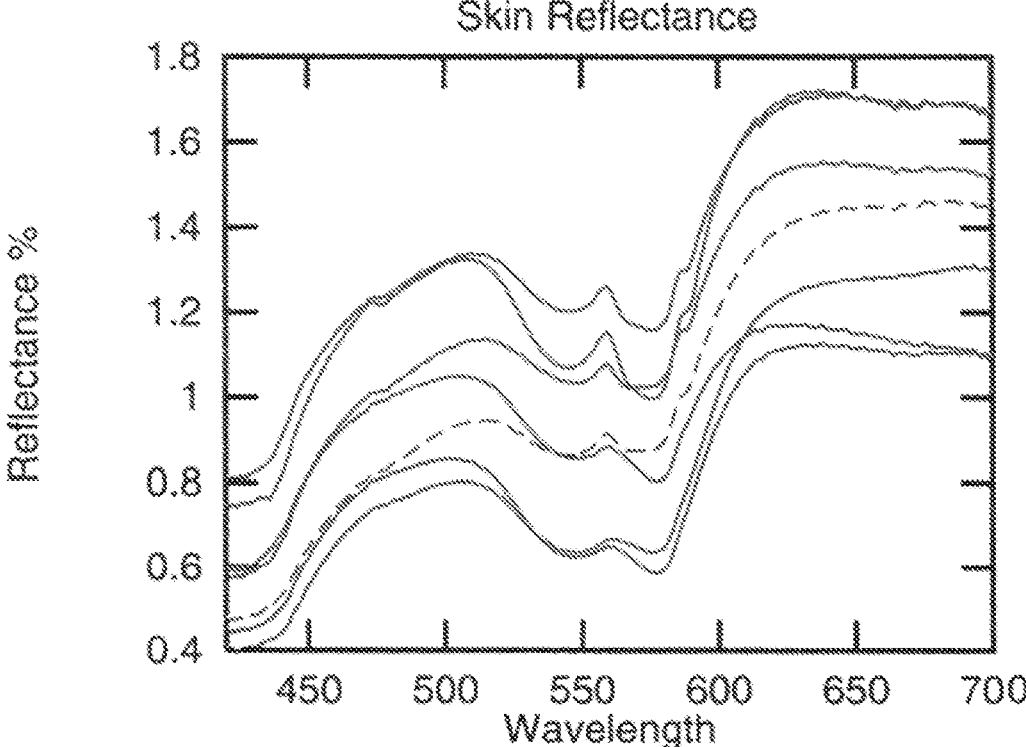
FIG. 2 shows examples of spectra of the back of a hand, taken from "The Reflectance Spectrum of Human Skin" by Elli Angelopoulou (https://repository.upenn.edu/cgi/viewcontent.cgi?article=1616&context=cis_reports)

With reference to FIG. 2, a photodiode with, for example, three LEDs deployed alongside it, may be used to detect three different wavelength PPG signals operating in reflection mode (although the skilled person will appreciate that transmission mode may alternatively be used). The wavelengths used may correspond to green, red and infra-red light. Each PPG (the AC signal) "sits" on top of a DC level whose value varies depending upon the light detector (e.g. photodiode) is looking at and what the wavelength is. For example, if one looks at the reflection spectrum of the back of the hand, as shown in FIG. 2, one can see large variations and signatures.

The signature shown in FIG. 2 comprises a "W" shape at around 550 nm which is characteristic of cartilage in the hand. The change in reflectance between the green wavelength (at 550 nm, or more generally 495-570 nm) and the red wavelength (at 650 nm, or more generally 620-750 nm) results in a reflectance increase of nearly 100%. Hence, if one takes the ratio of DC$_{green}$ to DC$_{red}$, the ratio would (under normal conditions) be less than unity (e.g. in FIG. 2 it is approximately equal to 0.8). A value of the ratio that is less than 1 provides a good indication that one is sensing the skin, but that is not a certainty. As discussed above, to determine whether the cap (and sensor) are fitted correctly, an additional technique (or modality) may be required.

Figure 3:
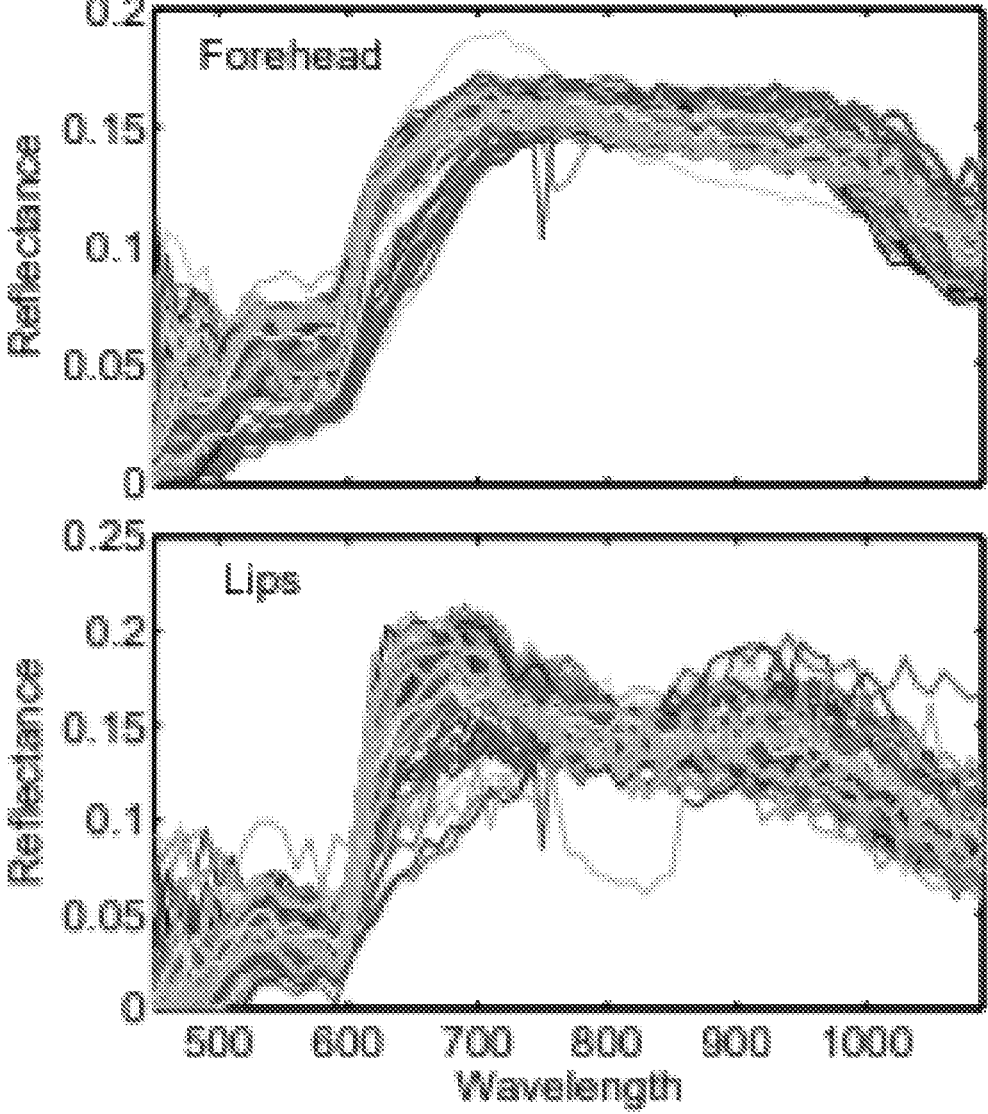
FIG. 3 shows an example of a reflection spectrum from the head compared to the lips, taken from "Is spectral reflectance of the face a reliable biometric?" by Muhammad Uzair et al (https://doi.org/10.1364/OE.23.015160)

FIG. 3 shows a reflection spectrum again, but this time other parts of the human body, namely that of the forehead and the lips. Particularly for the spectra relating to the forehead, the characteristic "W" is no longer present. However, in this case, there is a significant change in the DC reflection signal between green (at 550 nm) and red (at 650 nm). Here the ratio of DC$_{green}$ to DC$_{red}$ (or DC$_{infra\text{-}red}$>900 nm) is now only approximately equal to 0.4 (or more generally, between 0.3 and 0.5). In addition to the specific values discussed above, a significant difference (e.g. more than 20%) between DC$_{green}$ and DC$_{red}$, or between DC$_{red}$ and DC$_{infra\text{-}red}$, is another good indication the skin is being sensed (in this case, the forehead), but again that is not a certainty. Again, an additional technique (or modality) may be used to remove any false negatives.

Figure 4:
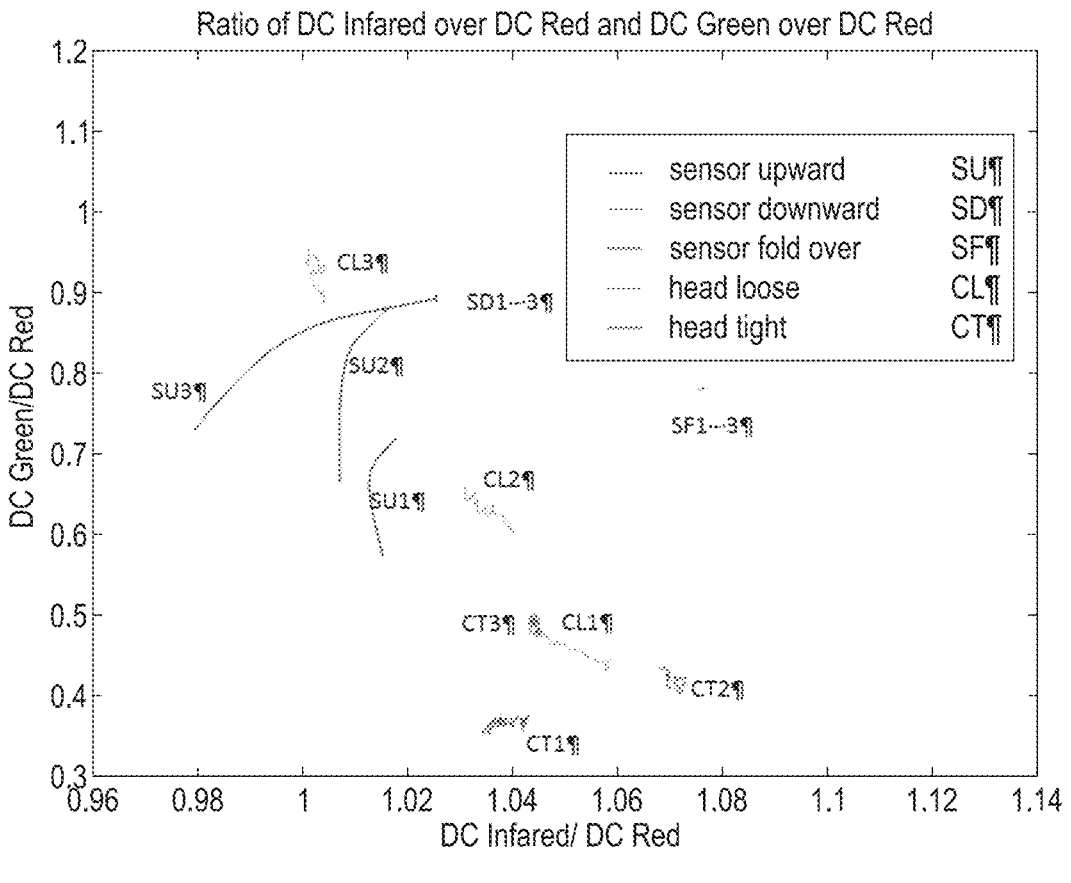
FIG. 4 shows an example of a DC ratio space for PPG sensor in five different scenarios.

With reference to FIG. 4, by way of an example of its use, a Surepulse PPG sensor integrated into a newborn (e.g. a neonate) hat (as described in WO 2017/149325) may be deployed in five different scenarios, namely: i) the sensor facing upwards towards room light (SU); ii) the sensor facing downwards on a desk top (SD); iii) the hat material folded over the sensor (SF); iv) the hat fitted loosely on a human forehead (CL); and v) the hat fitted tightly on a human forehead (CT).

FIG. 4 shows a plot of the resulting DC ratios of DC$_{infra\text{-}red}$ to DC$_{red}$ plotted against DC$_{green}$ to DC$_{red}$. For each scenario, three timed epoch average measurements may be made over 100 seconds (but, any value down to one second may be used) each with DC values sampled every 100 Hz. It can be seen that the SU, SD and SF occupy a completely different space from the tightly fitting hat (CT). On the other hand, the loosely fitted hat (CL) occupies a multitude of spaces. A tightly fitting hat (CT) may be identified from: a DC$_{green}$/DC$_{red}$<0.6; and/or a DC$_{infra\text{-}red}$/DC$_{red}$ between 1 and 1.1.

Hence, it may not only be possible to determine if the sensor is touching the human skin, it may be also be possible to assess if the hat is applied tightly or not.

Figure 5:
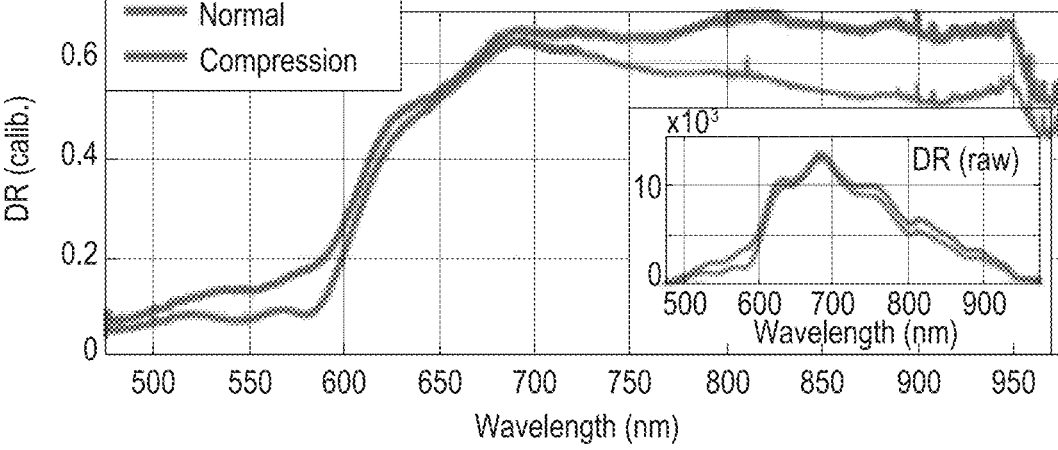
FIG. 5 shows an example of IR enhancement with compression, taken from "New insights into the origin of remote PPG signals in visible light and infrared" by Andreia V. Moço et al (https://doi.org/10.1038/s41598-018-26068-2)

With reference to FIG. 5, which shows diffuse reflectance (DR) vs wavelength, the spectrums of compressed and uncompressed skin illustrate that the ratio of $DC_{infra-red}$ to $DC_{green}$ also offers potential. This has been confirmed from experimental results of $DC_{green}$ to $DC_{red}$, and $DC_{green}$ to $DC_{infra-red}$. From these ratios, it may be possible to determine the optimum compression of the skin when combined with other features allowing a clear distinction of the optimum pressure.

Figures 16, 17:
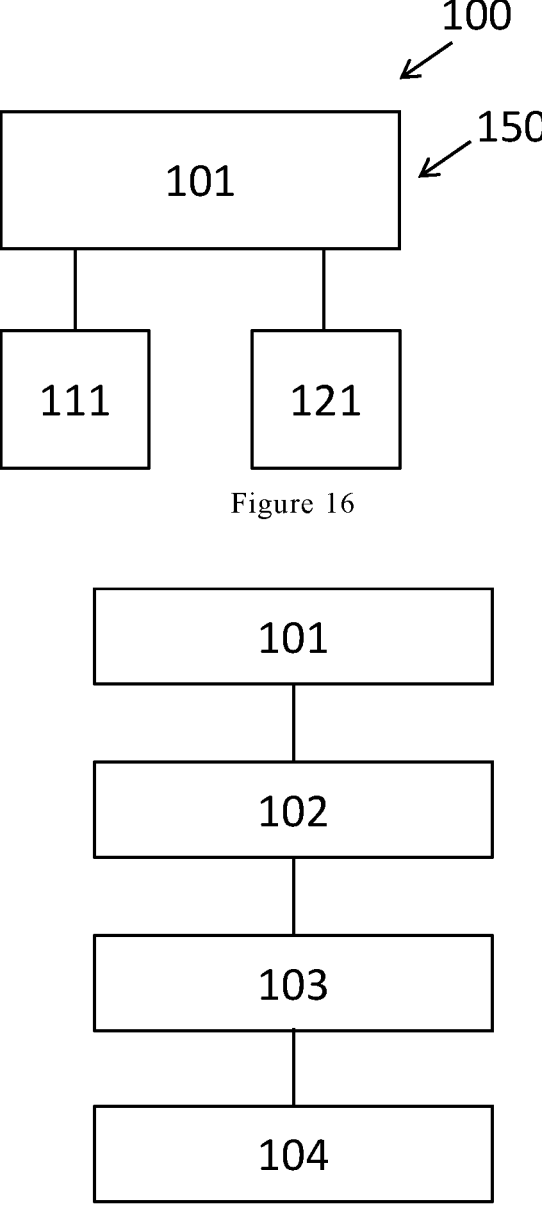
FIG. 16 shows an example embodiment of a device.
FIG. 17 shows an example method according to an embodiment.

FIG. 16 schematically illustrates an example embodiment following this approach, comprising an optical physiological sensor 100 comprising a processor 101, light emitter 111 and light detector 121. The light emitter 111 may comprise more than one light emitting element (e.g. emitting light with different wavelengths, such as red and green). The light detector 121 may comprise more than one light detecting element, and is configured to detect light from the light emitter 111 after it has been attenuated by tissue comprising blood vessels. In some embodiments, each light detecting element may be sensitive to a different wavelength. The processor 101 (which may be an embedded microprocessor) is configured receives a signal from the light detector 121 in response to the light detector 121 detecting light. The processor 101 is configured to determine a physiological parameter (such as $SpO_2$, as explained in the background section) from the signal (i.e. the detected light). The processor 101 is configured to implement a further measurement system 150, in which a DC light ratio of a non-varying component of detected light of a first wavelength and a second different wavelength after attenuation by the tissue is checked. As explained above, the DC ratio provides an indicator of whether an optical physiological sensor is properly placed on the tissue, so can indicate when an $SpO_2$ measurement (for example) is likely to be reliable.

2) The Detection of Human Capacitance

A capacitive electrode (e.g. a circulate plate) may be added to a device configured to measure PPG signals in order to determine if the device is in contact with the skin of the subject.

Figure 6:
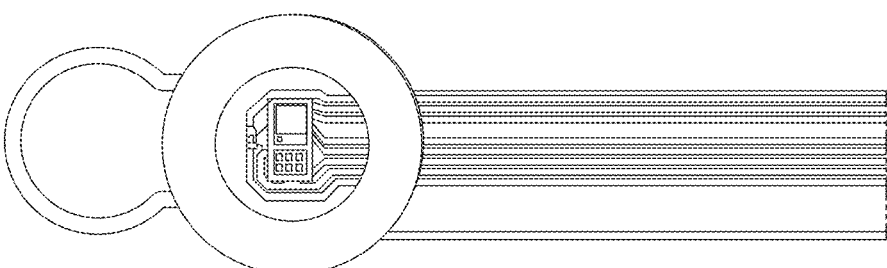
FIG. 6 shows a photograph of an example PPG sensor with a (yellow) circular capacitive sensor alongside.
Figure 7:
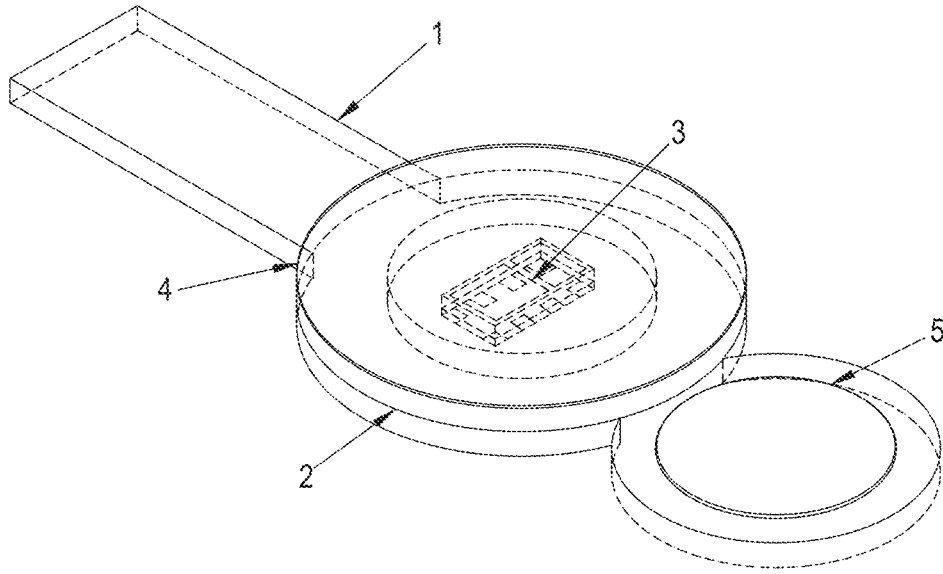
FIG. 7 shows a schematic of an example PPG sensor with additional capacitance sensor.

FIG. 6 is a photograph of an example PPG sensing device with a (yellow) circular capacitive sensor alongside the PPG sensor. An example schematic of the PPG sensing device that is shown in FIG. 6 is shown in FIG. 7. The PPG sensing device comprises a circular capacitance sensor 5 that is positioned alongside a PPG sensor 3.

Figure 8:
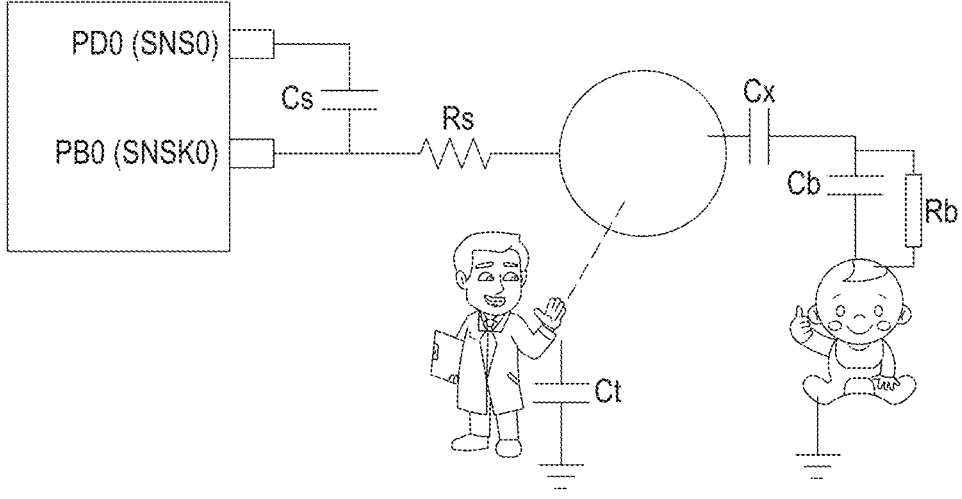
FIG. 8 shows a schematic of an example charging circuit (PDO) with a timer measuring charge rate (PBO) on a baby, and an approaching third party clinician with an additional capacitance.

With reference to FIG. 8, 'Cs' represents a user-set capacitance (typically 1 nf to 47 nF), 'Rs' represents a user-set resistance to adjust the charging-time range and sensitivity (typically 1 kΩ to 10 kΩ), 'Cx' represents the capacitance from the adjacent circular electrode (e.g. the circular capacitance sensor shown in FIGS. 6 and 7), 'Cb' represents the capacitance (or charge) naturally present on a human/animal test subject, 'Rb' represents the resistive component of the body (including Warburg impedances), and 'Ct' represents a third party human (such as a clinician) who may touch the sensor.

In particular, FIG. 8 shows results obtained from the deployment of a micro controller to charge the Cs, Rs, Cx and Cb path. Since Cs and Rs are known, the charging time (measured by a microprocessor timer) will reveal the combined value of Cx and Cb. The charging time may be determined repeatedly. Hence, numerous charging time values may be stored. Further, if Cx and Cb are touched by a third party (such as a clinician) having a capacitance of Ct, that capacitance is added in parallel. Hence, a different charging time may be calculated which is related this case to Cb+Ct.

Figure 9:
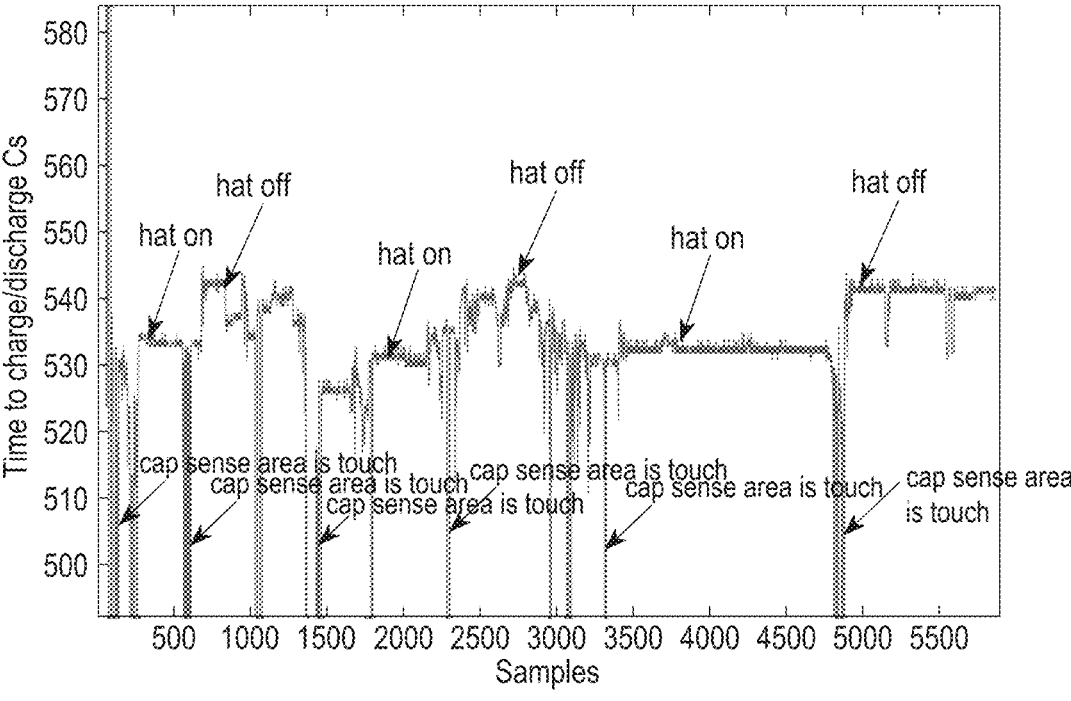
FIG. 9 shows the charging/discharging time of a circular electrode as a result of placing the cap on or off the head, or touching the sensor by a third party.

FIG. 9 shows sample results of the charge time as a function of three conditions, namely: i) the hat not on the head; ii) the hat on the head; and iii) the hat touched by a third party. Each of three conditions may be clearly differentiated by the resulting charge time which is labeled on the y-axis of FIG. 9. The charging time clearly enables differentiation as to when the hat is on or off the head, and whether a third party touches the hat.

Figure 10:
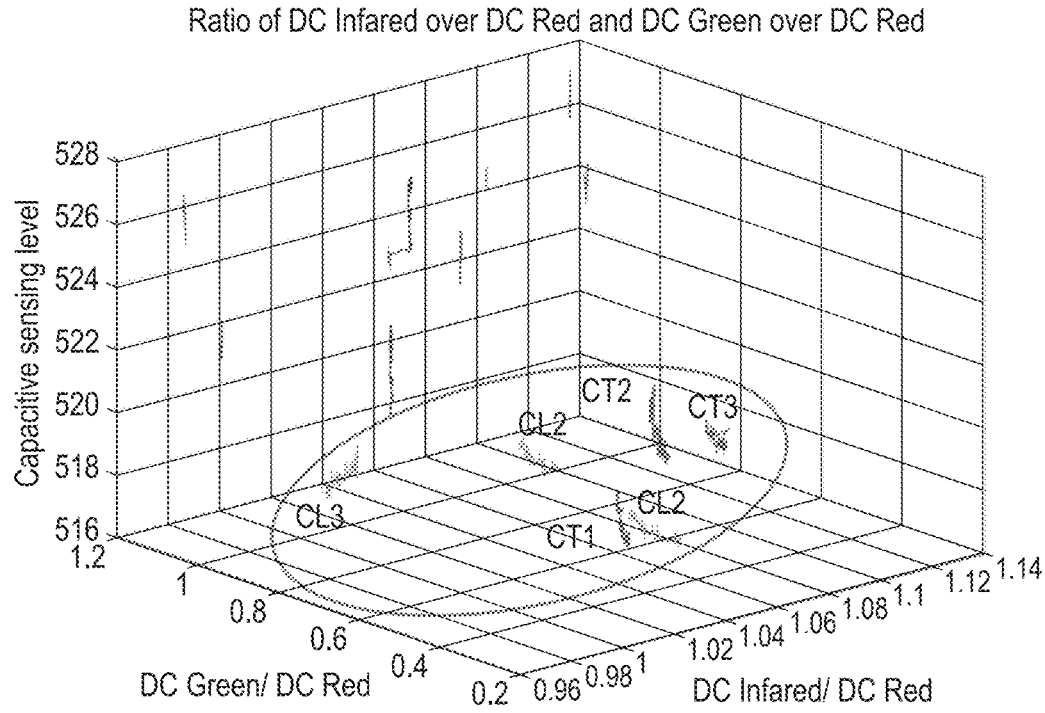
FIG. 10 shows an example of a 3D plot of DCgreen/DCred vs DCinfrared/DCred vs the capacitance sensing level in five different scenarios.

By combining the two results of capacitance charge time (Technique 2) and the DC ratios of light (Technique 1) a stronger differentiation may be seen between the conditions of the hat being on and the hat being off. The results are shown as a 3D plot in FIG. 10.

Although the combination of techniques 1 and 2 may be very useful in some settings, it may still not possible to differentiate between a loose and a tight fitting hat. Further, if the sensor is rocking, or even tilted, the combined result on its own may not suffice.

3) The Detection of a Change in Capacitance of a Sensor with Pressure

A pressure-sensitive capacitor (a capacitor whose capacitance value varies with applied pressure) may be disposed on the PPG-measuring device or adjacent thereto.

Figure 11:
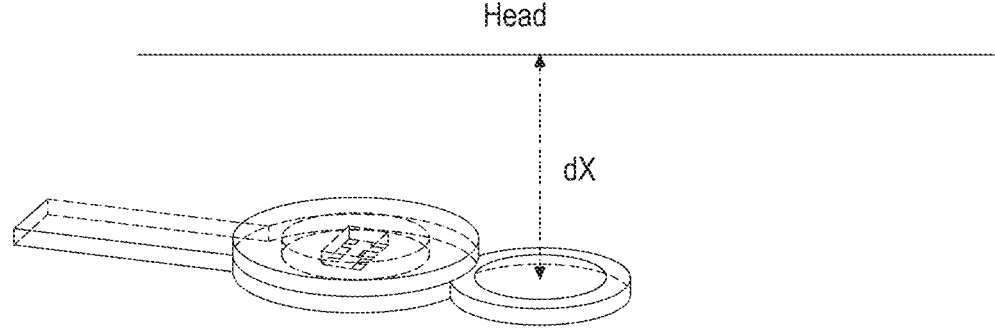
FIG. 11 shows an example of a separation between the PPG sensor and the head relating to the applied cap pressure using a circular electrode plate alongside a PPG sensor.

FIG. 11 shows an example schematic of a device with a lower electrode (e.g. a circular capacitive plate) and an air gap (between the lower electrode and the skin on a patient's head) used as the dielectric. That device may be similar or identical to the one employed in Technique 2. The capacitance may be further adjusted to suit a particular scenario by introducing a dielectric between the lower electrode and the patient's forehead. Such a dielectric, with a relative permittivity of $\varepsilon_r$, may result in a capacitance Cx equal to:

$$Cx = \frac{A.\varepsilon_0.\varepsilon_r}{dx}$$

where A=capacitance area; $\varepsilon_0$=permittivity of free space; and dx is the electrode-skin (head) separation.

Figure 12:
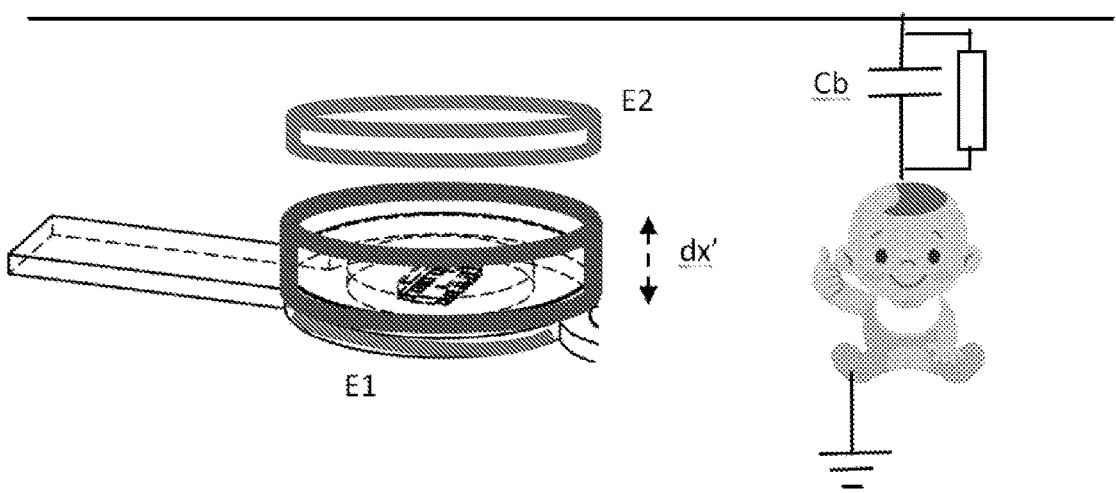
FIG. 12 shows an example of integrated electrodes with a compression based dielectric between them.

FIG. 12 shows an example of a variation on the device shown in FIG. 11. The device shown in FIG. 11 may be modified by introducing a compressible dielectric (blue), with a thickness of dx', and two conductive electrodes E1, E2 (red). The dielectric may be sandwiched between the two electrodes, and may comprise a foam or elastomeric material with a relative low modulus of elasticity (e.g. below 10 MPa). An advantage of this structure is that electrode E2 defines one of the electrodes rather than relying on the stratum corneum/epidermis (the skin) of the subject having to act as an electrode. The compression of the dielectric provides a non-linear adjustment of the capacitance (and charging time) as a function of the applied pressure. This enables an optimum pressure to be determined from the capacitance between E1 and E2 for the correct contact with the skin—neither too tight (resulting in occlusion and hence blanching) nor too loose (resulting in large movement artefacts).

The compressable dielectric layer dx' may comprise a number of different materials. The compressible dielelectic may comprise a polymeric elastomer. The polymeric elastomer may be which may be selected, manufactured, or tuned, to provide desired electrical properties and compressibility. The compressible dielectric may comprise poly(dimethylsiloxane) (PDMS), a silicone elastomer. The easy and efficient manipulation of PDMS may be desirable. The properties of PDMS, such as bio-compatibility and chemical inertness, may make it an appropriate choice for a PPG-measuring device (and other PPG-related scenarios).

A plurality of capacitive modules (an electrode pair sandwiching a pressure-sensitive dielectric) may be positioned at different locations on (or around) the PPG sensing device. For example, four separate capacitive modules may be positioned at "north', 'south', 'east' and 'west' locations on the PPG sensing device. Such an arrangement may allow the user or medic to determine which regions of the PPG sensing device are positioned correctly and which require adjustment. The skilled person will appreciate that other numbers and arrangements of capacitive modules may be desirable.

4) Force or Pressure Sensor

The addition of a force or pressure sensor on a PPG sensing device may provide contextual information to a user. Such a device is not limited to a capacitive sensor, and may comprise other transducers including piezoresistive, piezoelectric, and pressure responsive resistive materials. The force or pressure sensor may be positioned at or around the edge of the PPG sensor. An example material, such as that provided by Tekscan, may be customised into four separate force-detection regions, disposed at 'north', 'south', 'east' and 'west' locations on the PPG sensing device. The pressure applied at each of the four locations may provide the attending medical team with information on the overall pressure applied, allowing one to determine if the hat is too tight (and hence occluding the underlying skin, emptying the vessels under the skin of blood).

In addition, the presence of four force detection locations (e.g. piezoelectric etc) may allow the medical attendant to readjust the sensor when the forces are different as a result of a rocking or tilting of the sensor with respect to the skin of the patient.

Each force sensor may comprise two layers of conductive polymer separated by a layer of a pressure-sensitive fluid (which changes resistance between the two electrodes when subject to a pressure). The two layers may be laminated together using an adhesive. An advantage of this structure is that it may be thin and may be easily customised into the same footprint as the PPG sensor, and may allow for a window to be disposed in the centre through which light from the PPG sensor (or transmitted by, or reflected from the skin) may pass.

5) The Employment of Lens-Based Opto-Spatial Reduction

If motion occurs between the skin and the light source or detector, the micro and macro spatial variation of the skin may have a significant impact on recorded PPG (and DC) signal values.

Figure 13:
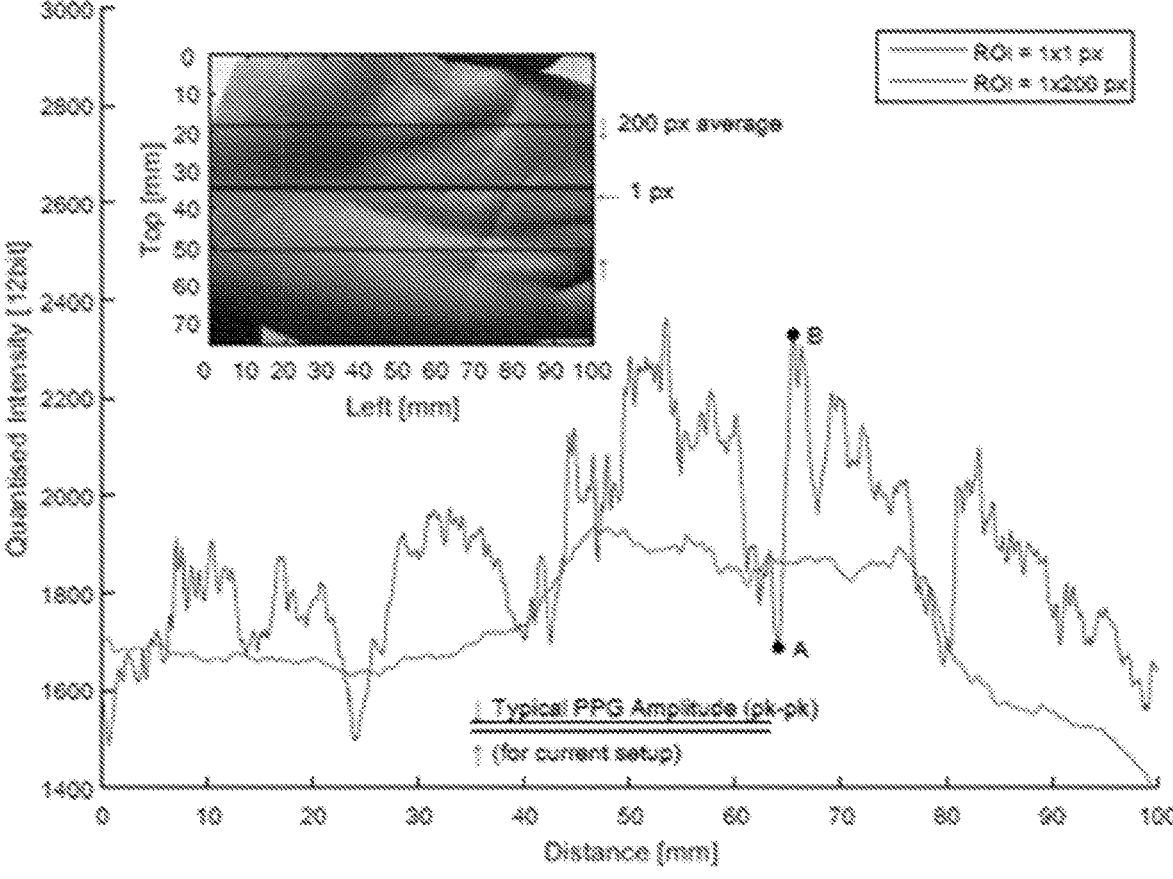
FIG. 13 shows an illustration of variations, as seen by a PixelFly camera, along both a single line and an average column of 200 pixels, on a person's palm.

With reference to FIG. 13, the DC variation in reflected light across the palm of the hand as illustrated, for example, by Butler M J (2016) (https://doi.org/10.1088/0967-3334137151N27). The skin's cellular structure, its variation in pigmentation and the underlying vascular networks all contribute to extreme perturbations in the measured amplitude of the light that is detected.

A lens may be introduced at each of the source and the detector of the PPG sensor. The lenses may not only focus and collect light efficiently (compared with a PPG sensor without a lens), but may also spatially average out DC variations in the signal by limiting and/or defining the region of interest (ROI). A focal region at the object/skin of around 1 mm (for example) may not completely remove large DC variations in the PPG signal, but the deployment of a lens greatly assists in doing so, and may improve the PPG signal that is measured.

The lens may be configured to protrude above the surface of the source and/or detector of the PPG sensor so that the lens may impinge on the skin of the subject. Such an arrangement may physically reduce the X and Y movements of the PPG sensing device with respect to the skin of the subject, and hence improve the accuracy and reliability of the measured PPG signal.

It may not be possible to determine, with a high degree of certainty, whether a hat (comprising a PPG sensor) is correctly fitted on the head of a new-born (neonate) using only one of Techniques 1-5. However, it has been shown that by combining any two or more of Techniques 1-5 it may, in fact, be possible to determine (with a high degree of certainty) whether the hat is fitted correctly and hence it may be possible to obtain accurate and reliable PPG signal measurements and $SpO_2$ determinations.

To reiterate, the certain embodiments may provide the attending team with contextual information that may allow the adjustment of the hat, for example in terms of the tightness to avoid occlusion by the optical sensor and tilting of the optical sensor. In addition, the motion detection may allow rogue data to be provided with a confidence flag or removed during $SpO_2$ measurements. A log of the motion derived from at least one of the techniques described herein (and preferably employing at least two of the methods) may allow significant post processing assistance.

Figure 14:
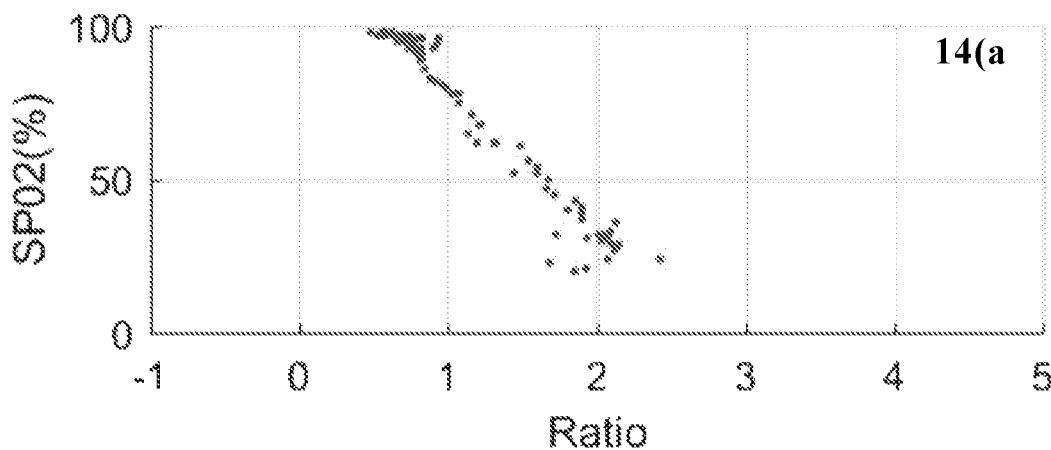
FIG. 14 shows example calibration curves relating the ratio R to a measured SpO2 value determined from PPG data obtained according to an embodiment, using only PPG data that is indicated to be reliable.
Figure 14:
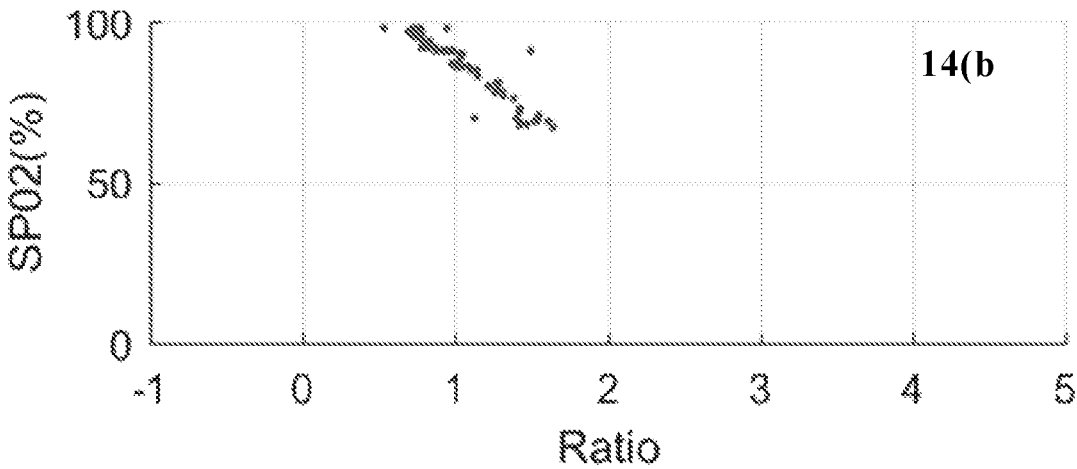

FIGS. 14a and 14b show results for two newborns, showing the R value obtained from PPG measurements obtained from a hat similar to that disclosed in WO 2017/149325. The value of SpO2 (on the y-axis) is obtained from a sensor on the newborn's wrist. R values (on the x-axis) were obtained from a hat mounted optical sensor held in contact with the forehead of the newborn by the hat. The optical sensor comprises green, red and IR light emitters and is configured to determine $DC_{green}/DC_{red}$ and/or $DC_{green}/DC_{IR}$ ratios (as discussed above), and also comprises capacitive sensor for detecting when the optical sensor is in proper contact with the skin. The PPG values in FIGS. 14a and 14b have been selected to be those that are likely to be reliable, by selecting DC ratios that are stable and low, and selecting capacitance values that are stable and indicative of proper contact.

It can be seen that selecting PPG measurements that are likely to be reliable (based on further measurement modalities) produces a highly linear calibration curve for relating R to SpO2.

Figure 15:
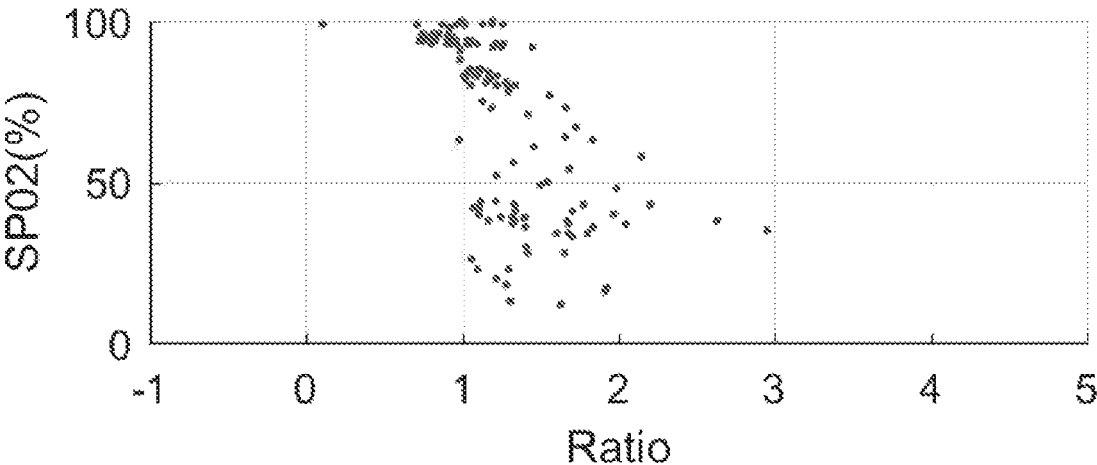
FIG. 15 shows an example calibration curve relating the ratio R to a measured SpO2 value determined from PPG data obtained without filtering values to select only those that are indicated to be reliable.

FIG. 15 shows a similar R-curve obtained without filtering of the PPG measurements to select those likely to be reliable. It can be seen from FIG. 15 that there is a relatively large scatter and poor linearity.

FIG. 17 shows a method according to an example embodiment, comprising steps 101 to 104. At step 101, a portion of tissue of a subject is illuminated (e.g. with red light and green light). At step 102 light from the illumination is detected after is has been attenuated with tissue (the tissue comprising blood vessels). At step 103, an optical physiological measurement is determined from the detected light, for example $SpO_2$ or heart rate. At step 104, a further measurement system (e.g. as described above) is used to determine whether the physiological measurement (determined in step 103) is likely to be reliable.

Although specific examples have been discussed, it will be appreciated that variations are possible within the scope of the invention, which should be determined with reference to the accompanying claims. Variations are intentionally within the scope of the claims.

What is claimed is:

1. A device comprising:
   an optical physiological sensor, wherein the optical physiological sensor comprises a light emitter and a light detector configured to detect the light from the light emitter after it has been attenuated by tissue comprising blood vessels, and the optical physiological sensor is configured to determine the value of a physiological parameter from the detected light; and
   a further measurement system configured to determine when the value of the physiological parameter is likely to be reliable, the further measurement system comprising at least one measurement subsystem, each employing a different measurement modality that is also different to a measurement modality used to determine the value of the physiological parameter; wherein
   the at least one measurement subsystem comprises a measurement subsystem configured to determine a DC light ratio of a non-varying component of detected light of a first wavelength and a second different wavelength after attenuation by the tissue; wherein
   the device is configured to determine an optimum pressure of the device against the tissue using the DC light ratio.

2. The device of claim 1, wherein the at least one measurement subsystem comprises at least a first and a second measurement subsystem.

3. The device of claim 1, wherein the first wavelength corresponds with green light, and the second wavelength corresponds with red light or infra-red light.

4. The device of claim 1, wherein the at least one measurement system comprises a measurement system that includes a capacitive sensor having an electrode configured to come into contact with the tissue.

5. The device of any of claim 4, wherein the capacitive sensor comprises a pressure-sensitive capacitive sensor.

6. The device of claim 5, wherein the pressure-sensitive capacitive sensor comprises a pair of electrodes and a compressible dielectric sandwiched between the electrodes.

7. The device of claim 5, wherein the capacitive sensor comprises a plurality of capacitive sensors, wherein each of the capacitive sensors is disposed at a different location proximate the optical physiological sensor.

8. The device of claim 1, wherein the at least one measurement system comprises a measurement subsystem that includes a pressure or force sensor.

9. The device of claim 8, wherein the pressure or force sensor comprises a plurality of pressure or force sensors, each disposed at a different location around the optical physiological sensor.

10. The device of claim 1, comprising a detector lens between the light detector and the tissue, and an illumination lens between the light emitter and the tissue.

11. The device of claim 1, wherein optical physiological sensor comprises a photoplethysmogram (PPG) sensor and/or a pulse oximeter.

12. The device claim 1, wherein the light emitter comprises a plurality of light-emitting diodes (LEDs) and/or the light detector comprises a photodiode.

13. A hat comprising:
   an optical physiological sensor, wherein the optical physiological sensor comprises a light emitter and a light detector configured to detect the light from the light emitter after it has been attenuated by tissue comprising blood vessels, and the optical physiological sensor is configured to determine the value of a physiological parameter from the detected light; and
   a further measurement system configured to determine when the value of the physiological parameter is likely to be reliable, the further measurement system comprising at least one measurement subsystem, each employing a different measurement modality that is also different to a measurement modality used to determine the value of the physiological parameter;
   wherein the hat is configured to retain the optical physiological sensor in contact with the forehead of a patient; wherein
   the at least one measurement subsystem comprises a measurement subsystem configured to determine a DC light ratio of a non-varying component of detected light of a first wavelength and a second different wavelength after attenuation by the tissue; wherein
   the device is configured to determine an optimum pressure of the device against the tissue using the DC light ratio.

14. The hat of claim 13, wherein the hat is sized to fit a neonate.

15. A method of determining an optical physiological measurement with a photoplethysmography device, comprising:
   illuminating a portion of tissue;
   detecting light after it has been attenuated by the tissue; and
   determining the optical physiological measurement from the detected light;
   using at least one further measurement system to determine when the physiological measurement is likely to be reliable, comprising:
      determining a DC light ratio of a non-varying component of detected light of a first wavelength and a second different wavelength after attenuation by the tissue; and
      determining an optimum pressure of the device against the tissue using the DC light ratio.

16. The method of claim 15, wherein the optical physiological measurement comprises a PPG or SpO2 measurement.

17. The method of claim 15, wherein using the further measurement system comprises at least one of:
   i) using a capacitive sensor to detect proper contact with the tissue;
   ii) using a pressure sensor to detect proper contact.

18. The method of claim 15, wherein a detector lens is disposed between a light detector and the tissue, and an illumination lens is disposed between a light emitter and the tissue.

19. The method of claim 15, further comprising automatically indicating or flagging whether the optical physiological measurement can be trusted in dependence on an output from the further measurement system.

* * * * *